United States Patent
Liao et al.

(10) Patent No.: US 11,668,706 B2
(45) Date of Patent: *Jun. 6, 2023

(54) NEAR-INFRARED II POLYMER FLUORESCENT MICROSPHERE AND METHOD FOR PREPARING SAME

(71) Applicants: NIRMIDAS BIOTECH, INC., Palo Alto, CA (US); WWHS BIOTECH, INC., Guangdong (CN)

(72) Inventors: Tao Liao, Shenzhen (CN); Guoxin Wang, Shenzhen (CN); Meijie Tang, Shenzhen (CN); Qinglai Yang, Shenzhen (CN); Su Zhao, Shenzhen (CN); Yongye Liang, Shenzhen (CN)

(73) Assignee: WWHS BIOTECH, INC., Guangdong (CN)

( * ) Notice: Subject to any disclaimer, the term of this patent is extended or adjusted under 35 U.S.C. 154(b) by 214 days.

This patent is subject to a terminal disclaimer.

(21) Appl. No.: 16/632,889

(22) PCT Filed: Nov. 6, 2017

(86) PCT No.: PCT/CN2017/109556
§ 371 (c)(1),
(2) Date: Jan. 22, 2020

(87) PCT Pub. No.: WO2019/019472
PCT Pub. Date: Jan. 31, 2019

(65) Prior Publication Data
US 2020/0181485 A1    Jun. 11, 2020

(30) Foreign Application Priority Data

Jul. 24, 2017 (CN) .......................... 201710607567.9
Jul. 24, 2017 (CN) .......................... 201710607934.5
Jul. 24, 2017 (CN) .......................... 201710608436.2

(51) Int. Cl.
*G01N 33/533*  (2006.01)
*G01N 33/543*  (2006.01)
(Continued)

(52) U.S. Cl.
CPC .............. *G01N 33/533* (2013.01); *C08J 9/16* (2013.01); *C08J 9/28* (2013.01); *C09K 11/025* (2013.01);
(Continued)

(58) Field of Classification Search
CPC ....... C09K 11/025; C09K 11/06; C09K 11/88; C09K 11/7492; C09K 11/661;
(Continued)

(56) References Cited

FOREIGN PATENT DOCUMENTS

CN    102701265 A    10/2012
CN    103509552 A    1/2014
(Continued)

OTHER PUBLICATIONS

Search Report for European Application No. 17918703.4, dated Mar. 26, 2021, 12 pages.
(Continued)

*Primary Examiner* — C Melissa Koslow
(74) *Attorney, Agent, or Firm* — Squire Patton Boggs (US)

(57) ABSTRACT

Provided are a near-infrared II polymer fluorescent sub-microsphere and a method for preparing the same. The method includes steps of 1) dissolving fluorochrome in a water-immiscible organic solvent, thus obtaining a fluorochrome solution; 2) distributing a polymer sub-microsphere into a sodium dodecyl sulfonate solution, thus obtaining a sub-microsphere solution with the polymer sub-microsphere as a carrier for the fluorochrome; 3) subjecting a first mixture of the fluorochrome solution and the sub-microsphere solution to ultrasonic treatment, thus obtaining an emulsion; 4)

(Continued)

swelling the emulsion such that the fluorochrome solution enters nanopores formed during swelling of the polymer sub-microsphere, thus obtaining a second mixture; and 5) heating the second mixture to volatilize the organic solvent, such that the fluorochrome is crystallized out and encapsulated in the nanopores, thus obtaining the near-infrared II polymer fluorescent sub-microsphere.

17 Claims, 6 Drawing Sheets

(51) Int. Cl.
| | |
|---|---|
| G01N 33/544 | (2006.01) |
| G01N 33/558 | (2006.01) |
| C08J 9/16 | (2006.01) |
| C08J 9/28 | (2006.01) |
| C09K 11/02 | (2006.01) |
| C09K 11/06 | (2006.01) |
| C09K 11/74 | (2006.01) |
| C09K 11/66 | (2006.01) |
| C09K 11/88 | (2006.01) |
| C09K 11/65 | (2006.01) |
| B82Y 20/00 | (2011.01) |
| B82Y 30/00 | (2011.01) |
| B82Y 40/00 | (2011.01) |

(52) U.S. Cl.
CPC ............. *C09K 11/06* (2013.01); *C09K 11/65* (2013.01); *C09K 11/661* (2013.01); *C09K 11/7492* (2013.01); *C09K 11/88* (2013.01); *G01N 33/544* (2013.01); *G01N 33/54346* (2013.01); *G01N 33/558* (2013.01); *B82Y 20/00* (2013.01); *B82Y 30/00* (2013.01); *B82Y 40/00* (2013.01); *C08J 2325/06* (2013.01); *C09K 2211/1051* (2013.01)

(58) Field of Classification Search
CPC .... C09K 11/65; C09K 2211/1051; C08J 9/16; C08J 9/28; C08J 2325/06
See application file for complete search history.

(56) References Cited

FOREIGN PATENT DOCUMENTS

| | | |
|---|---|---|
| CN | 105126714 A | 12/2015 |
| CN | 105693906 A | 6/2016 |
| WO | 0113120 A1 | 2/2001 |

OTHER PUBLICATIONS

Chen et al., Direct water-phase synthesis of lead sulfide quantum dots encapsulated by β-lactoglobulin for in vivo second near infrared window imaging with reduced toxicity, Royal Society of Chemistry, ChemComm, Feb. 2016, vol. 52, pp. 4025-4028.

Huang et al., "Development of NIR-II fluorescence image-guiding and pH-responsive nanocapsules for cocktail drug delivery", Nano Research, 2015, vol. 8, No. 6, pp. 1932-1943.

Qian et al., "Multicolor polystyrene nanospheres tagged with up-conversion fluorescent nanocrystals", Nanotechnology, 2006, vol. 19, 4 pages.

Tao et al., "Biological Imaging Using Nanoparticles of Small Organic Molecules with Fluorescence Emission at Wavelengths Longer than 1000 nm**", Angewandte Communications, 2013, vol. 52, p. 13002-13006.

Yang et al., "Rational Design of Molecular Fluorophores for Biological Imaging in the NIR-II Window", Advanced Materials, 2017, vol. 29, 9 pages.

WPI Database, Jun. 22, 2016, AN 2016-426627, XP002802352, 2 pages.

International Search Report and Written Opinion for Application No. PCT/CN2017/109556, dated Apr. 18, 2018, 17 pages.

A                               B

A                               B

NEAR-INFRARED II POLYMER FLUORESCENT MICROSPHERE AND METHOD FOR PREPARING SAME

CROSS-REFERENCE TO RELATED APPLICATIONS

The present application is a National Phase of International Application No. PCT/CN2017/109556, filed on Nov. 6, 2017, which claims priorities to and benefits of Chinese Patent Application Nos. 201710607567.9, 201710607934.5 and 201710608436.2, all filed with the China National Intellectual Property Administration (CNIPA) of the People's Republic of China on Jul. 24, 2017, the entire contents of which are incorporated herein by reference

FIELD

The present disclosure relates to the field of biotechnology, in particular to a near-infrared II polymer fluorescent sub-microsphere and a method for preparing the same.

BACKGROUND

A polymer fluorescent sub-microsphere, as a special function sub-microsphere, is capable of encapsulating tens of thousands to hundreds of thousands of fluorescent molecules for one sub-microsphere, such that labeling efficiency and resistance to photobleaching of the fluorescent molecules are both enhanced, thereby improving sensitivity of fluorescence detection greatly. Besides, the polymer fluorescent sub-microsphere is allowed to be modified from the outside with one or more functional groups (such as a carboxy group, an amino group and an aldehyde group) in a very flexibly way, which benefits for covalent coupling to a proteins (such as an antibody) and improvement of stability and labeling efficiency of an labeling agent. At present, the polymer fluorescent sub-microsphere has been widely used in labeling, tracing, detecting, imaging, enzyme immobilizing, medical immunology, high-throughput drug screening and so on. However, the traditional polymer fluorescent sub-microsphere emits lights merely in a visible region with an emitting wavelength below 780 nm, resulting in poor penetrability and intense background fluorescence when applied in imaging of living organisms, cells or tissues, diagnosing in vitro, and so on. Meantime, since the traditional polymer fluorescent sub-microsphere is generally with low quantum efficiency and relative closer interval (around 20 nm) between an exciting wavelength and an emitting wavelength, which results in poor analysis sensitivity, there exits high demand on a color filter for the fluorescence detection.

Therefore, there is still a need to improve the polymer fluorescent sub-microsphere and the method for preparing the same.

SUMMARY

Embodiments of the present disclosure seek to solve at least one of the problems existing in the related art to at least some extent. An object of the present disclosure is to provide a near-infrared II polymer fluorescent sub-microsphere and a method for preparing the same. In a simple and rapid way, the near-infrared II polymer fluorescent sub-microsphere is prepared with high quantum efficiency, and strong penetrability and low background interference during the fluorescence detection, thereby having promising prospects in terms of the live imaging, biolabeling detection and so on.

In a first aspect, the present disclosure provides in embodiments a method for preparing a near-infrared II polymer fluorescent sub-microsphere, comprising the following steps of:

1) dissolving fluorochrome in a water-immiscible organic solvent, thus obtaining a fluorochrome solution;

2) distributing a polymer sub-microsphere into a sodium dodecyl sulfonate solution, thus obtaining a sub-microsphere solution with the polymer sub-microsphere as a carrier for the fluorochrome;

3) subjecting a first mixture of the fluorochrome solution and the sub-microsphere solution to ultrasonic treatment, thus obtaining an emulsion;

4) swelling the emulsion such that the fluorochrome solution enters nanopores formed during swelling of the polymer sub-microsphere, thus obtaining a second mixture; and 5) heating the second mixture to volatilize the organic solvent, such that the fluorochrome is crystallized out and encapsulated in the nanopores, thus obtaining the near-infrared II polymer fluorescent sub-microsphere, wherein the near-infrared II polymer fluorescent sub-microsphere obtained by steps 1) to 5) results in emitting a wavelength in a range of 1000 nm to 1700 nm under an excitation light less than 1000 nm.

In some embodiments of the present disclosure, the fluorochrome emits a wavelength in a range of 1000 nm to 1700 nm under an excitation light less than 1000 nm.

In some embodiments of the present disclosure, the fluorochrome is selected from the group consisting of organic molecules including those shown as formula (I), formula (II) or formula (III), or carbon nanotubes, or PbS, PbSe or InAs quantum dots, or rare earth nanoparticles.

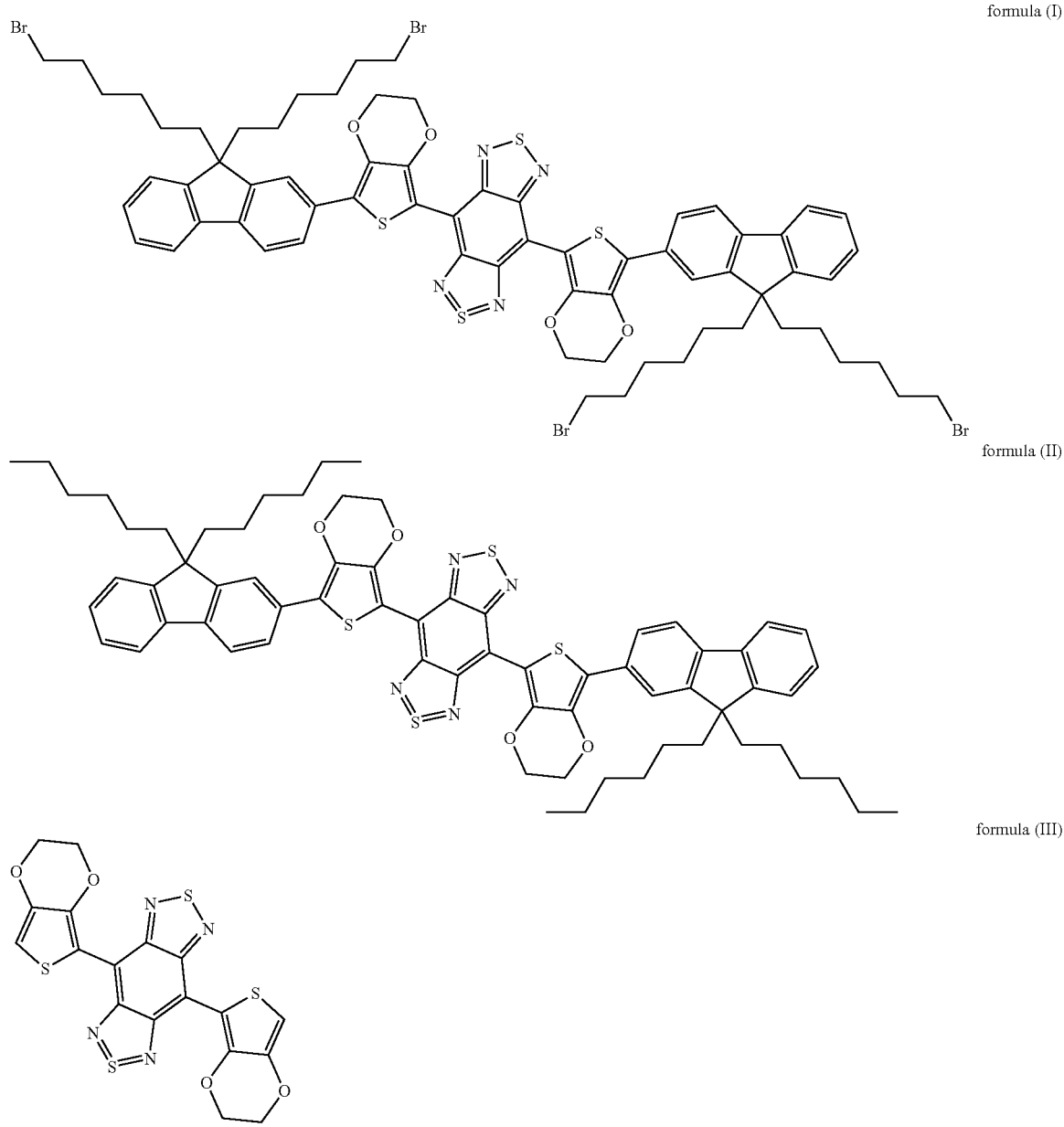 [SMILES: BrCCCCCCC1(CCCCCCBr)c2ccccc2-c2ccc(-c3sc(-c4c5c(c(-c6sc(-c7ccc8c(c7)C(CCCCCCBr)(CCCCCCBr)c7ccccc7-8)c7c6OCCO7)c6nsnc46)N=S=N5)c4c3OCCO4)cc21 ; CCCCCCC1(CCCCCC)c2ccccc2-c2ccc(-c3sc(-c4c5c(c(-c6sc(-c7ccc8c(c7)C(CCCCCC)(CCCCCC)c7ccccc7-8)c7c6OCCO7)c6nsnc46)N=S=N5)c4c3OCCO4)cc21 ; c1sc(-c2c3c(c(-c4scc5c4OCCO5)c4nsnc24)N=S=N3)c2c1OCCO2]

formula (I)

formula (II)

formula (III)

In some embodiments of the present disclosure, the fluorochrome in the fluorochrome solution has a concentration of 1 mg/ml to 50 mg/ml, so that the polymer sub-microsphere is capable of encapsulating more fluorochrome, thereby further improving sensitivity of fluorescence detection.

In some embodiments of the present disclosure, the organic solvent is at least one selected from the group consisting of ethyl acetate, dichloromethane, trichloromethane, 1,2-dichloroethane and aromatic hydrocarbons, preferably dichloromethane.

In some embodiments of the present disclosure, the polymer sub-microsphere is at least one selected from the group consisting of polystyrene sub-microsphere, poly (methyl methacrylate) sub-microspheres, polyformaldehyde sub-microspheres and poly (lactic acid-co-glycolic acid) sub-microspheres, which can be well distributed in an aqueous solution and allows to be modified at its surface with different radicals in a flexible way, thereby facilitating to subsequent coupling. Therefore, the near-infrared II polymer fluorescent sub-microsphere can be obtained with strong penetrability, low background interference and excellent dispersibility in an aqueous solution.

In some embodiments of the present disclosure, the polymer sub-microsphere has a particle size of 20 nm to 1000 nm, so that the polymer sub-microsphere is capable of encapsulating more fluorochrome, thereby further improving sensitivity of fluorescence detection.

In some embodiments of the present disclosure, in the step 2), the polymer sub-microsphere is distributed into the sodium dodecyl sulfonate solution in a mass/volume ratio of 10 mg/ml to 200 mg/ml, thereby not only guaranteeing the polymer sub-microsphere to well disperse in the sodium dodecyl sulfonate solution, but also allowing the polymer sub-microsphere to be fully in contact with dichloromethane during the subsequent swelling, such that the polymer sub-microsphere can be swelled to a maximal extent.

In some embodiments of the present disclosure, the first mixture includes the fluorochrome solution and the sub-microsphere solution in a volume ratio of 1:5 to 1:20, such that dichloromethane is in a proper amount for swelling the polymer sub-microsphere thoroughly, thus further increasing encapsulation efficiency and enhancing weight of the near-infrared II polymer fluorescent sub-microsphere.

In some embodiments of the present disclosure, in the step 3), the first mixture includes the fluorochrome solution and the sub-microsphere solution in a volume ratio of 1:5 to 1:20. In some embodiments of the present disclosure, in the step 3), the first mixture includes the fluorochrome and the polymer sub-microsphere in a mass ratio of 0.1:100 to 30:100. Therefore, each sub-microsphere is capable of encapsulating tens of thousands to hundreds of thousands of fluorescent molecules, thereby improving sensitivity of fluorescence detection greatly.

In some embodiments of the present disclosure, in the step 4), the emulsion is swelled at 10° C. to 50° C. under stirring for 1 hour to 10 hours, such that the polymer sub-microsphere can be swelled sufficiently in the presence of dichloromethane, which ensures the fluorochrome entering nanopores formed during swelling of the polymer sub-microsphere successfully.

In some embodiments of the present disclosure, in the step 5), the second mixture is heated at a temperature of 50° C. to 90° C., such that dichloromethane can be volatilized completely in a short time period.

In a second aspect, the present disclosure provides in embodiments a near-infrared II polymer fluorescent sub-microsphere prepared by the method described in the first aspect.

In a third aspect, the present disclosure provides in embodiments a near-infrared II polymer fluorescent sub-microsphere, including hydrophobic fluorochrome and a polymer sub-microsphere, wherein the fluorochrome is encapsulated in nanopores of the polymer sub-microsphere, and the polymer sub-microsphere is of hydrophobic moiety inside and hydrophilic moiety outside; and the near-infrared II polymer fluorescent sub-microsphere emits a wavelength in a range of 1000 nm to 1700 nm under an excitation light less than 1000 nm.

In some embodiments of the third aspect, the fluorochrome of the near-infrared II polymer fluorescent sub-microsphere is selected from the group consisting of organic molecules including those shown as formula (I), formula (II) or formula (III), or carbon nanotubes, or PbS, PbSe or InAs quantum dots, or rare earth nanoparticles.

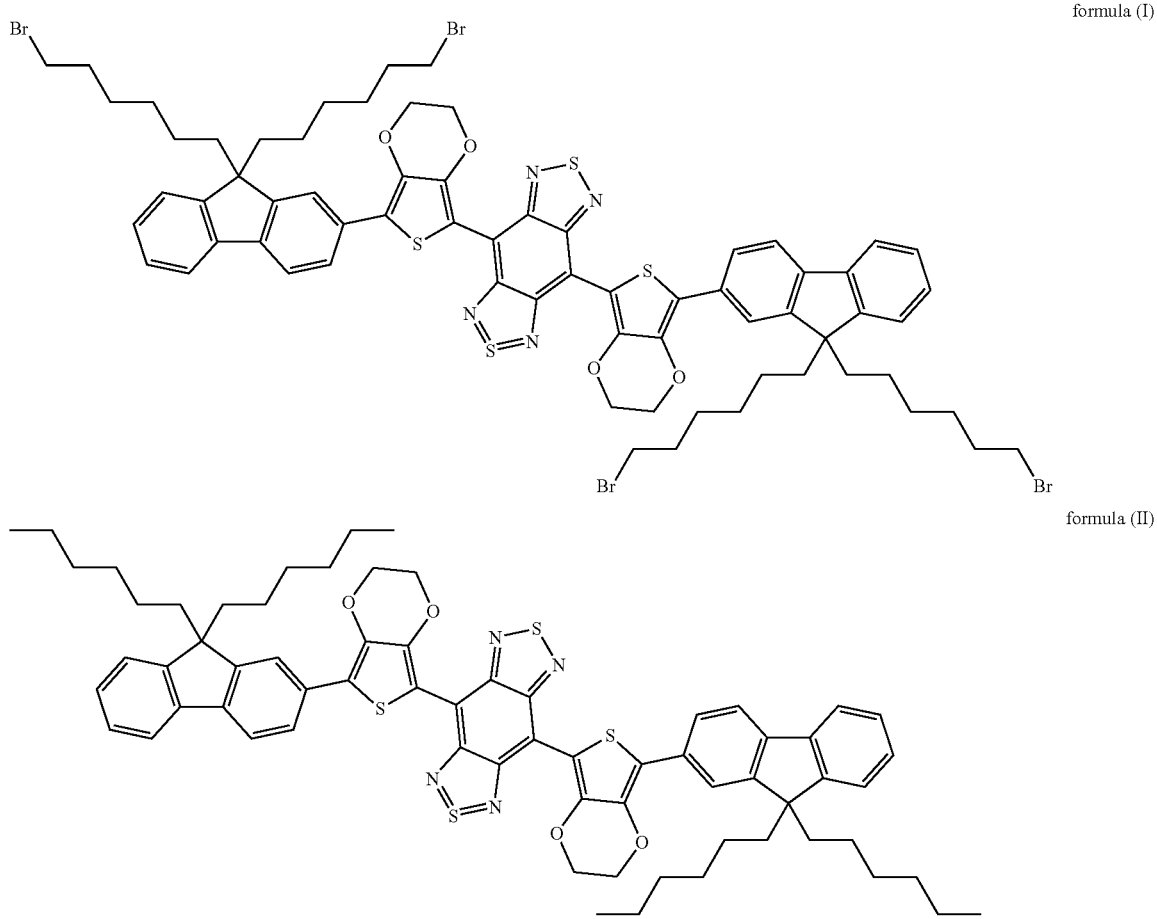

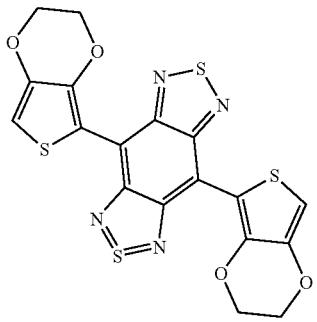

formula (III)

In some embodiments of the third aspect, the polymer sub-microsphere is at least one selected from the group consisting of polystyrene sub-microspheres, poly (methyl methacrylate) sub-microspheres, polyformaldehyde sub-microspheres and poly(lactic acid-co-glycolic acid) sub-microspheres.

In some embodiments of the third aspect, the polymer sub-microsphere is in a size range of 20 nm to 1000 nm.

According to embodiments of the present disclosure, the near-infrared II polymer fluorescent sub-microsphere prepared has advantageous characteristics of good dispersibility, high quantum efficiency up to 25%, relative broader interval between an exciting wavelength less than 1000 nm, such as at 740 nm and an emitting wavelength at 1000 nm to 1700 nm, and strong penetrability and low background interference during the fluorescence detection, thus dramatically magnifying a fluorescent signal and improving sensitivity of the fluorescence detection. Therefore, the near-infrared II polymer fluorescent sub-microsphere prepared can be used in live imaging, biolabeling detection and so on with promising prospects.

DESCRIPTION OF DRAWINGS

FIG. 3(A), FIG. 3(B), and FIG. 3(C) show absorption spectrums of and fluorescence spectrums emitted respectively by fluorochrome represented by formula (I), (II) or (III) which is contained in near-infrared II polymer fluorescent sub-microspheres according to embodiments of the present disclosure.

FIG. 4(A), FIG. 4(B), and FIG. 4(C) are WO graphs showing fluorescent signals during immunochromatography detection of procalcitonin (PCT) in serum using near-infrared II polymer fluorescent sub-microspheres according to embodiments of the present disclosure.

FIG. 6(A), FIG. 6(B), and FIG. 6(C) show scanning electron microscope photographs of carboxylic polystyrene pellets and carboxylic polystyrene fluorescent sub-microspheres according to embodiments of the present disclosure.

FIG. 7(A), FIG. 7(B), and FIG. 7(C) show fluorescent photographs and fluorescent spectrums of carboxylic polystyrene fluorescent sub-microspheres under irradiation with excitation light at a wavelength of 740 nm according to embodiments of the present disclosure.

DETAILED DESCRIPTION

Figure 1:
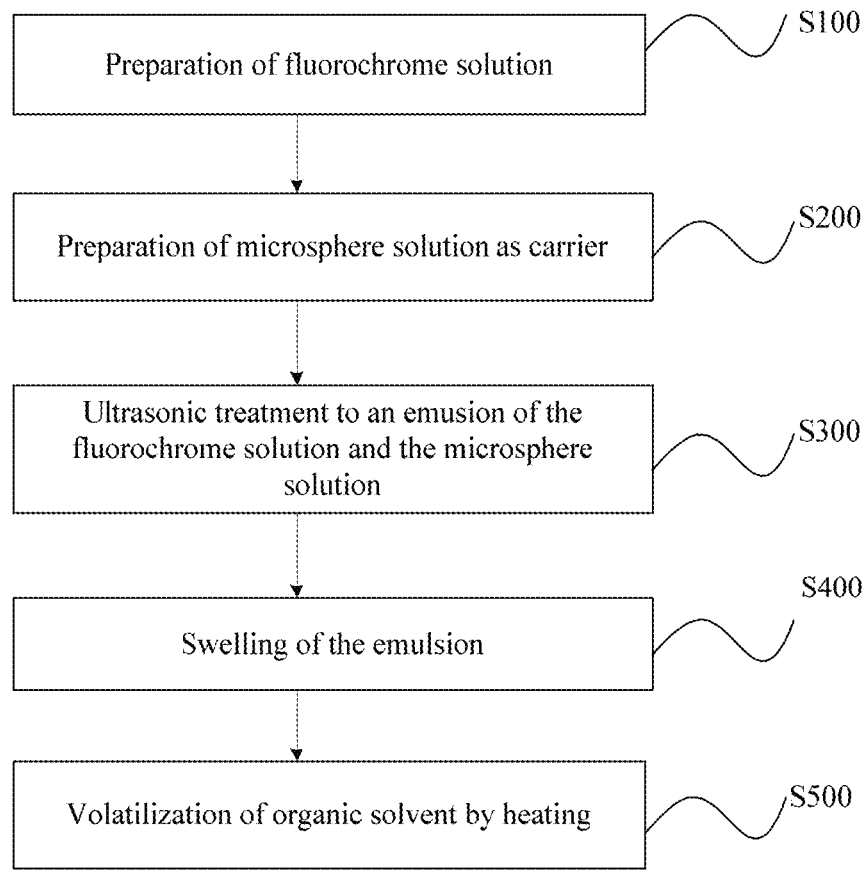
FIG. 1 is a flow chart showing a method for preparing a near-infrared II polymer fluorescent sub-microsphere according to embodiments of the present disclosure.

Embodiments of the present disclosure are described in detail below, and exemplary embodiments are shown in the drawings. Throughout the description, like or similar reference numerals refer to like or similar elements or elements having the same or similar functions. The embodiments described below with reference to the drawings are exemplary, and they are intended to be illustrative of the disclosure and are not to be construed to limit the disclosure.

The present disclosure is accomplished by the present inventors based on the following discoveries.

Because of disadvantageous characteristics of poor penetrability and intense background fluorescence, low quantum efficiency and relative closer interval between an exciting wavelength and an emitting wavelength, the existing method for fluorescence detection using the traditional polymer fluorescent sub-microsphere is in low sensitivity and with high demand on a color filter used. The near-infrared fluorescent sub-microsphere, especially the near-infrared II fluorescent sub-microsphere has advantageous characteristics of strong penetrability and low background interference during the fluorescence detection, thereby having promising prospects in terms of live imaging, biolabeling detection and so on. However, there is few near-infrared II polymer fluorescent sub-microsphere being found so far, and it has not been reported about preparation of the near-infrared II polymer fluorescent sub-microsphere.

With great efforts to solve the above deficiencies, the present inventors find that near-infrared II fluorochrome selected from the group consisting of organic molecules including those shown as formula (I), formula (II) or formula (III), or carbon nanotubes, or PbS, PbSe or InAs quantum dots, or rare earth nanoparticles, with advantageous characteristics such as a long penetrating distance (several millimetres) and low background interference, can replace the conventional near-infrared fluorescent sub-microsphere for application in imaging of living organisms, cells or tissues, diagnosing in vitro, and so on. Nevertheless, the fluorochrome as described above cannot be directly applied in live imaging because of strong hydrophobicity per se, and thus requiring Hydrophilic modification in advance, which not only involves tedious processes, but also provides a modified fluorochrome with significantly decreased quantum efficiency after dissolved in the aqueous solution, thus causing an adverse effect to sensitivity of the fluorescence detection. In order to overcome the above disadvantages, the present inventors surprisingly find that the method including encapsulating the fluorochrome as described above within the polymer sub-microsphere by swelling achieves a desirable effect with high quantum efficiency of 25% or more and good dispersibility in an aqueous solution, thereby facilitating labeling detection of various biological macromolecule.

In one aspect, the present disclosure provides in embodiments a method for preparing a near-infrared II polymer fluorescent sub-microsphere, comprising steps of 1) dissolving fluorochrome in a water-immiscible organic solvent, thus obtaining a fluorochrome solution; 2) distributing a polymer sub-microsphere into a sodium dodecyl sulfonate solution, thus obtaining a sub-microsphere solution with the polymer sub-microsphere as a carrier for the fluorochrome; 3) subjecting a first mixture of the fluorochrome solution and the sub-microsphere solution to ultrasonic treatment, thus obtaining an emulsion; 4) swelling the emulsion such that the fluorochrome solution enters nanopores formed during swelling of the polymer sub-microsphere, thus obtaining a second mixture; and 5) heating the second mixture to volatilize the organic solvent, such that the fluorochrome is crystallized out and encapsulated in the nanopores, thus obtaining the near-infrared II polymer fluorescent sub-microsphere. In some embodiments, the fluorochrome is selected from the group consisting of organic molecules including those shown as formula (I), formula (II) or formula (III), or carbon nanotubes, or PbS, PbSe or InAs quantum dots, or rare earth nanoparticles.

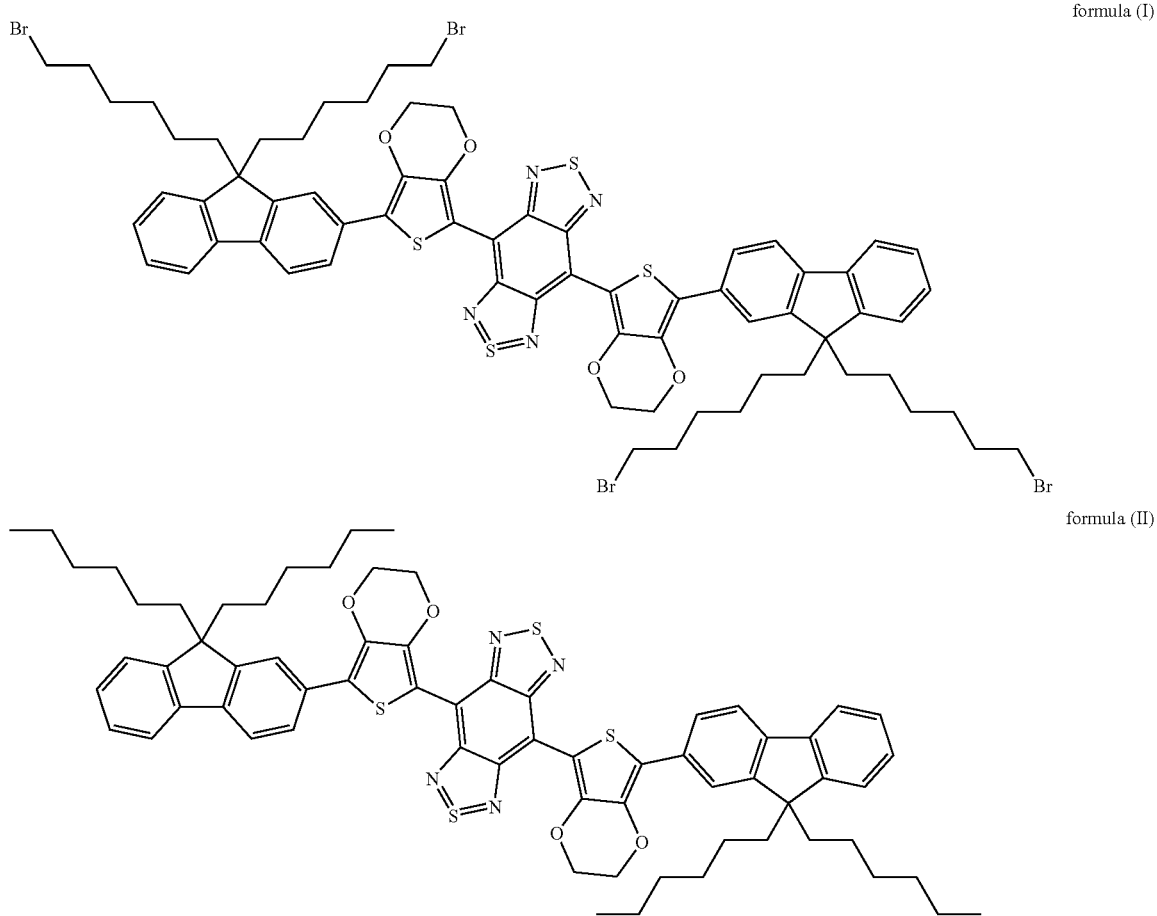

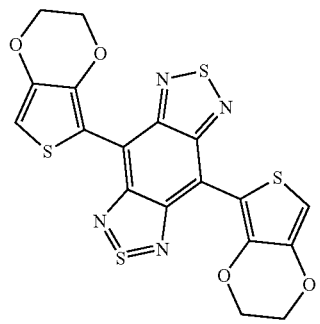

formula (III)

According to the method for preparing the near-infrared II polymer fluorescent sub-microsphere in embodiments described above, the fluorochrome is dissolved in the organic solvent at first, thus obtaining the fluorochrome solution; meanwhile the polymer sub-microsphere is distributed into the sodium dodecyl sulfonate solution, thus obtaining a sub-microsphere solution with the polymer sub-microsphere as a carrier for the fluorochrome; subsequently the first mixture of the fluorochrome solution and the sub-microsphere solution is subjected to ultrasonic treatment, swelling and heating, such that the fluorochrome can be successfully encapsulated in the sub-microsphere, thus obtaining the near-infrared II polymer fluorescent sub-microsphere.

According to the embodiments described above, in a simple and rapid way, the near-infrared II polymer fluorescent sub-microsphere is prepared with good dispersibility in an aqueous solution, high quantum efficiency up to 25%, and relative broader interval between an exciting wavelength less than 1000 nm, such as at 740 nm and an emitting wavelength at 1000 nm to 1700 nm. As a result, such a method not only overcomes difficulties of directly applying the fluorochrome selected from the group consisting of organic molecules including those shown as formula (I), formula (II) or formula (III), or carbon nanotubes, or PbS, PbSe or InAs quantum dots, or rare earth nanoparticles to live imaging owing to strong hydrophobicity, but also provides the near-infrared II polymer fluorescent sub-microsphere with strong penetrability and low background interference during the fluorescence detection, which can extremely magnify the fluorescent signal and thus improve the sensitivity of the fluorescence detection, thereby having promising prospects in terms of live imaging, biolabeling detection and so on.

Figure 2:
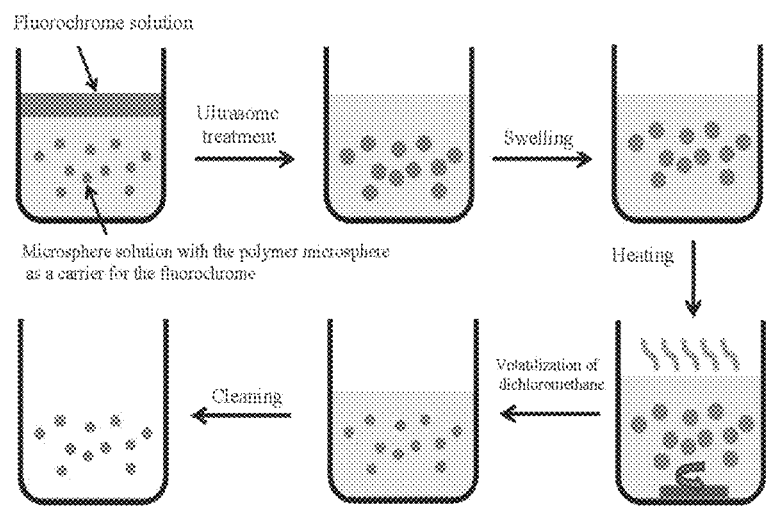
FIG. 2 is a flow chart showing a method for preparing a near-infrared II polymer fluorescent sub-microsphere according to other embodiments of the present disclosure.

The method for preparing the near-infrared II polymer fluorescent sub-microsphere is described in detail with reference to FIG. 1 to FIG. 2.

S100: Preparation of a Fluorochrome Solution

According to some embodiments of the present disclosure, fluorochrome is dissolved in a water-immiscible organic solvent, thus obtaining the fluorochrome solution. According to some embodiments of the present disclosure, the fluorochrome is selected from the group consisting of organic molecules including those shown as formula (I), formula (II) or formula (III), or carbon nanotubes, or PbS, PbSe or InAs quantum dots, or rare earth nanoparticles.

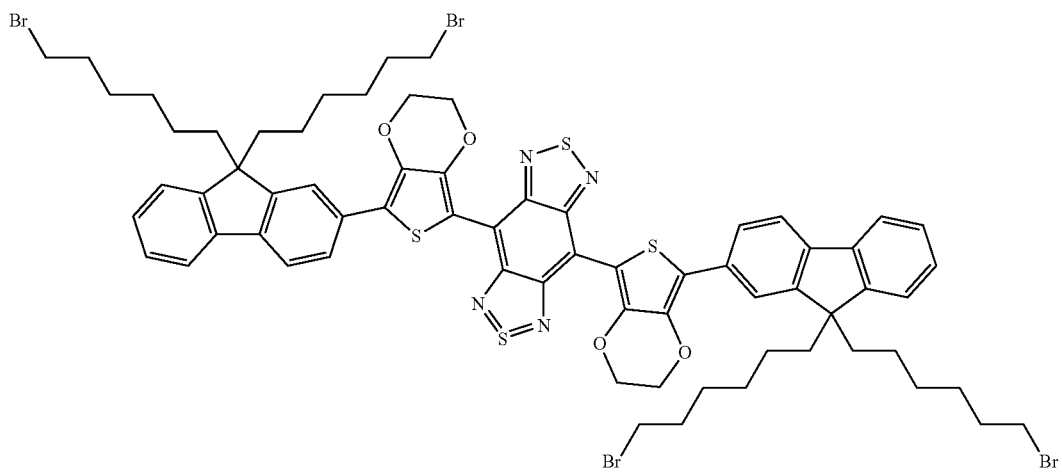

formula (I)

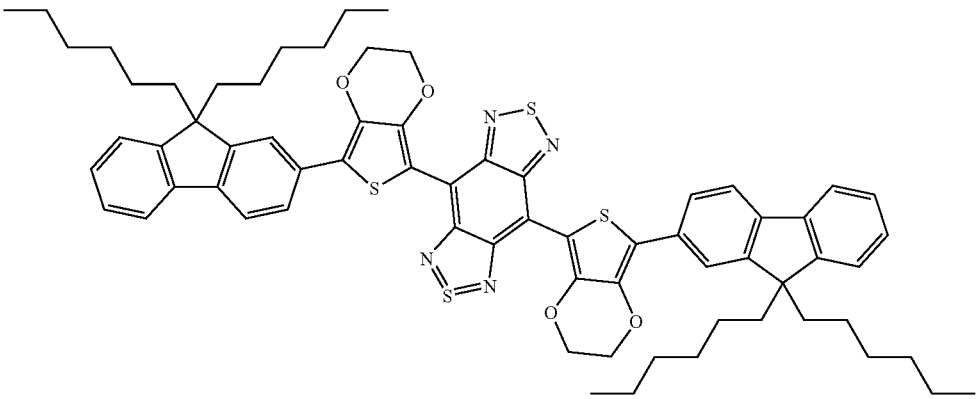

formula (II)

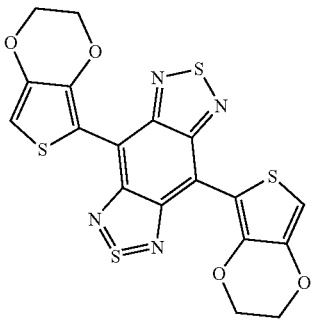

formula (III)

In embodiments of the present disclosure, the formula (I) is 4,8-(5-(9,9-di(6-bromohexyl)-9H-fluoren-2-yl)-2,3-dihydrothieno[3,4-b][1,4]dioxine)-1H,5H-benzo[1,2-c:4,5-c']bis([1,2,5]thiadiazole); the formula (II) is 4,8-(5-(9,9-dihexyl-9H-fluoren-2-yl)-2,3-dihydrothieno[3,4-b][1,4]dioxine)-1H,5H-benzo[1,2-c:4,5-c']bis([1,2,5]thiadiazole); and the formula (III) is 2,3-dihydrothieno[3,4-b][1,4]dioxine)-1H,5H-benzo[1,2-c:4,5-c']bis([1,2,5]thiadiazole).

Figure 3:
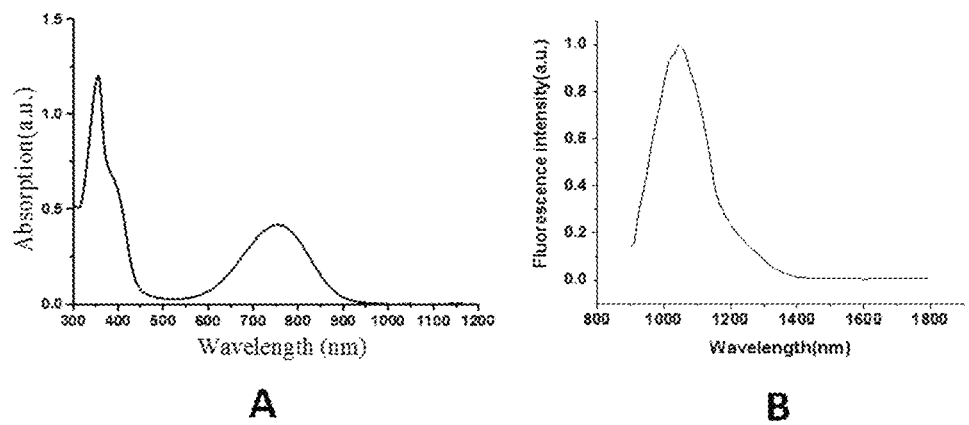
FIG. 3(A)—parts A and B—show absorption and fluorescence intensity as a function of wavelength.
FIG. 3(B)—parts A and B—show absorption and emission as a function of wavelength.
FIG. 3(C)—parts A and B—show absorption and emission as a function of wavelength.
Figure 3:
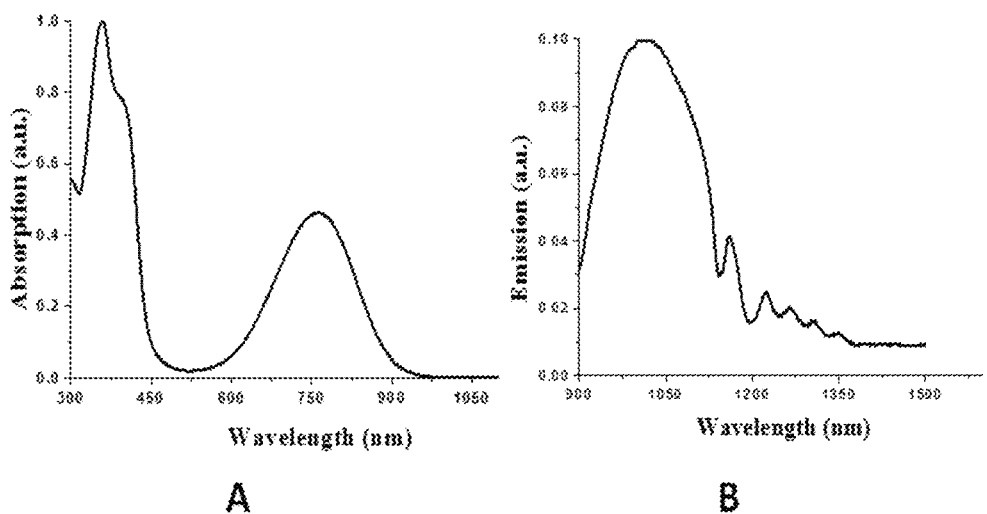
Figure 3:
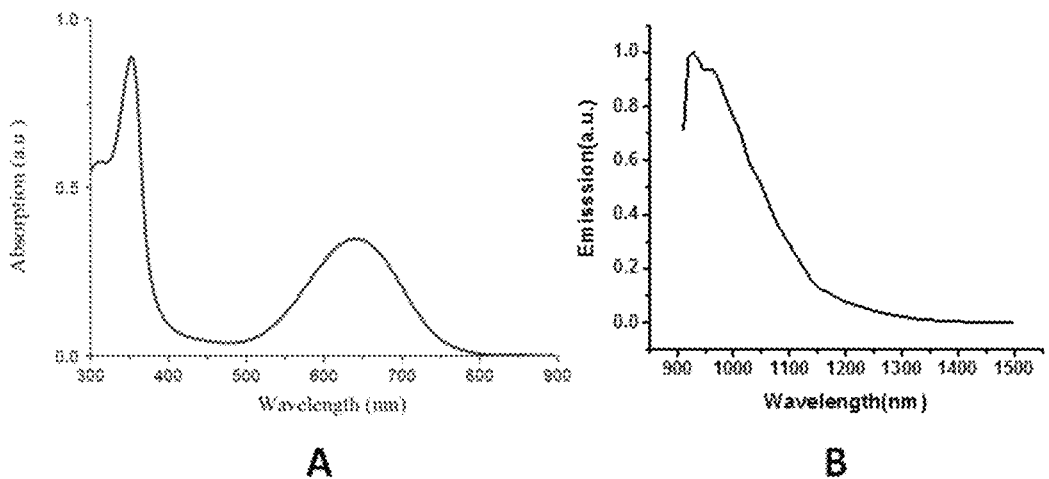

In some embodiments of the present disclosure, the fluorochrome selected from the group consisting of organic molecules including those shown as formula (I), formula (II) or formula (HI), or carbon nanotubes, or PbS, PbSe or InAs quantum dots, or rare earth nanoparticles is used to prepare a near-infrared II polymer fluorescent sub-microsphere. As shown in FIGS. 3(a) to 3(c), absorption spectrums of and fluorescence spectrums emitted respectively by the fluorochrome of formulas (I) to (III), the inventors find that the fluorochrome has strong absorption to light less than 1000 nm, such as at 365 nm and 740 nm, and emits fluorescence between 1000 nm and 1700 nm. Accordingly, because of the relative broader interval between the exciting wavelength and the emitting wavelength, the fluorochrome has many advantageous characteristics such as strong penetrability (penetration distance of several millimeters) and low background interference in the live imaging application. Therefore, the present near-infrared II polymer fluorescent sub-microsphere prepared with the fluorochrome has advantageous characteristics such as strong penetrability and low background interference during the fluorescence detection, thereby having promising prospects in terms of live imaging, biolabeling detection and so on.

According to some embodiments of the present disclosure, the fluorochrome in the fluorochrome solution has a concentration between 1 mg/ml to 50 mg/ml, specifically 1 mg/ml to 10 mg/ml, 10 mg/ml to 20 mg/ml, 20 mg/ml to 30 mg/ml, 30 mg/ml to 40 mg/ml or 40 mg/ml to 50 mg/ml, for example, 1 mg/ml, 10 mg/ml, 20 mg/ml, 30 mg/nil, 40 mg/ml or 50 mg/ml, preferably 20 mg/ml, so that the polymer sub-microsphere is capable of encapsulating more fluorochrome, and thus the present near-infrared II polymer fluorescent sub-microsphere prepared emits the fluorescence with higher intensity during the fluorescence detection, thereby further improving sensitivity of the fluorescence detection.

In some embodiments of the present disclosure, the organic solvent is at least one selected from the group consisting of ethyl acetate, dichloromethane, trichloromethane, 1,2-dichloroethane and aromatic hydrocarbons, In an example of the present disclosure, dichloromethane, so that dichloromethane can further facilitate swelling of the polymer sub-microsphere, thereby further increasing encapsulating efficiency of the fluorochrome.

S200: Preparation of a Sub-Microsphere Solution

In some embodiments of the present disclosure, a polymer sub-microsphere is distributed into a sodium dodecyl sulfonate solution, thus obtaining the sub-microsphere solution with the polymer sub-microsphere as a carrier for the fluorochrome.

In some embodiments of the present disclosure, the polymer sub-microsphere is at least one selected from the group consisting of polystyrene sub-microspheres, poly (methyl methacrylate) sub-microspheres, polyformaldehyde sub-microspheres and poly (lactic acid-co-glycolic acid) sub-microspheres. Such a polymer sub-microsphere is capable of encapsulating tens of thousands to hundreds of thousands of fluorescent molecules in one sub-microsphere and preventing the hydrophobic fluorochrome mentioned above from leaking out owing to a hydrophobic moiety inside the polymer sub-microsphere; and is capable of well dispersing in the aqueous solution due to a charge or hydrophilic moiety outside the polymer sub-microsphere. Therefore, the near-infrared II polymer fluorescent sub-microsphere, with advantageous characteristics such as strong penetrability and low background interference during the fluorescence detection, can be prepared with such the polymer sub-microsphere.

In some embodiments of the present disclosure, the polymer sub-sub-microsphere has a particle size of 20 nm to 1000 nm, specifically 20 nm to 100 nm, 100 nm to 200 nm, 200 nm to 300 nm, 300 nm to 400 nm, 400 nm to 500 nm, 500 nm to 600 nm, 600 nm to 700 nm, 700 nm to 800 nm, 800 nm to 900 nm or 900 nm to 1000 nm, for example, 20 nm, 50 nm, 100 nm, 150 nm, 200 nm, 250 nm, 300 nm, 350 nm, 400 nm, 450 nm, 500 nm, 550 nm, 600 nm, 650 nm, 700 nm, 750 nm, 800 nm, 850 nm, 900 nm, 950 nm or 1000 nm, preferably 850 nm. Accordingly, the polymer sub-microsphere is capable of encapsulating more fluorochrome, such that the near-infrared II polymer fluorescent sub-microsphere prepared can have higher intensity of the fluorescence, thereby further improving sensitivity of fluorescence detection.

In some embodiments of the present disclosure, the sodium dodecyl sulfonate (SDS) solution is of a concentration of 0.1% to 0.8%, for example 0.2% to 0.6%, eg., 0.25%, such that the SDS solution as an emulsifier not only guarantees the polymer sub-microspheres to be better dispersed in the SDS solution, but also facilitates obtaining a uniform emulsion during the subsequent ultrasonic treatment.

In some embodiments of the present disclosure, the present polymer sub-microsphere is distributed into the sodium dodecyl sulfonate solution in a mass/volume ratio of 10 mg/ml to 200 mg/ml, specifically 10 mg/ml to 50 mg/ml, 50 mg/ml to 100 mg/ml, 100 mg/ml to 150 mg/ml or 150 mg/ml to 200 mg/ml, for example, 10 mg/ml, 30 mg/ml, 50 mg/ml, 70 mg/ml, 100 mg/ml, 120 mg/ml, 150 mg/ml, 170 mg/ml or 200 mg/ml, preferably 30 mg/ml, which not only enhances yield of the near-infrared II polymer fluorescent sub-microsphere effectively, but also allows the polymer sub-microspheres to be swelled to a maximal extent in the next step, such that the polymer sub-microsphere is capable of encapsulating more fluorochrome, and thus the present near-infrared II polymer fluorescent sub-microsphere prepared emits the fluorescence with higher intensity during the fluorescence detection, thereby further improving sensitivity of fluorescence detection.

S300: Ultrasonic Treatment

In some embodiments of the present disclosure, a first mixture of the fluorochrome solution and the sub-microsphere solution is subjected to ultrasonic treatment, thus obtaining an emulsion.

In some embodiments of the present disclosure, the first mixture includes the fluorochrome solution and the sub-microsphere solution in a volume ratio of 1:5 to 1:20, specifically 1:5, 1:8, 1:10, 1:12, 1:15, 1:17 or 1:20, preferably 1:10, such that dichloromethane is in a proper amount for swelling all of the polymer sub-microspheres thoroughly, and the fluorochrome solution is allowed to enter the nanopores formed during swelling of the polymer sub-microsphere completely, thus the polymer sub-microsphere is capable of encapsulating more fluorochrome and the high quality of near-infrared II polymer fluorescent sub-microsphere prepared by the present method emits the fluorescence with higher intensity during the fluorescence detection, thereby further improving sensitivity of fluorescence detection.

In some embodiments of the present disclosure, the first mixture includes the fluorochrome and the polymer sub-microsphere in a mass ratio of 0.1:100 to 30:100, specifically 0.1:100, 0.5:100, 1:100, 5:100, 7:100, 10:100, 12:100, 15:100, 20:100, 22:100, 25:100, 27:100 or 30:100, preferably 1:15. Thus, the fluorochrome and the polymer sub-microsphere are in such a proper matching ratio that availability of these raw material is improved and the fluorochrome solution is allowed to enter the nanopores formed during swelling of the polymer sub-microsphere completely, thus the polymer sub-microsphere is capable of encapsulating more fluorochrome and the near-infrared II polymer fluorescent sub-microsphere prepared by the present method emits the fluorescence with higher intensity during the fluorescence detection, thereby further improving sensitivity of fluorescence detection.

S400: Swelling of the Emulsion

In some embodiments of the present disclosure, the emulsion is swelled such that the fluorochrome solution enters nanopores formed during swelling of the polymer sub-microsphere, thus obtaining a second mixture.

The present inventors find that the fluorochrome selected from the group consisting of organic molecules including those shown as formula (I), formula (II) or formula (III), or carbon nanotubes, or PbS, PbSe or InAs quantum dots, or rare earth nanoparticles cannot be directly applied in live imaging because of strong hydrophobicity per se, and thus requiring Hydrophilic modification in advance, which not only involves tedious processes, but also provides a modified fluorochrome with significantly decreased quantum efficiency after dissolved in the aqueous solution. However, the polymer sub-microsphere used in the present disclosure is capable of encapsulating tens of thousands to hundreds of thousands of fluorescent molecules in one sub-microsphere and preventing the hydrophobic fluorochrome mentioned above from leaking out owing to a hydrophobic moiety inside the polymer sub-microsphere; and is capable of well dispersing in the aqueous solution due to a charge or hydrophilic moiety outside the polymer sub-microsphere. Besides, such a polymer sub-microsphere is allowed to be modified from the outside with various functional groups in a flexible way, which facilitates labeling of molecules such as proteins and DNAs. Accordingly, the present inventors provide the method including encapsulating the fluorochrome as described above within the polymer sub-microsphere by swelling to obtain the near-infrared II polymer fluorescent sub-microsphere with high quantum efficiency of 25% or more and good dispersibility in an aqueous solution, thereby facilitating labeling detection of various biological macromolecules.

In some embodiments of the present disclosure, the emulsion is swelled at 10° C. to 50° C. under stirring for 1 hour to 10 hours, specifically, at 10° C., 15° C., 20° C., 25° C., 30° C., 35° C., 40° C., 45° C. or 50° C., for 1 hour, 2 hours, 3 hours, 4 hours, 5 hours, 6 hours, 7 hours, 8 hours, 9 hours or 10 hours, preferably, at 40° C. for 6 hours, such that the polymer sub-microsphere can swell sufficiently in the presence of dichloromethane, which ensures the fluorochrome entering nanopores formed during swelling of the polymer sub-microsphere successfully, and thus the present near-infrared II polymer fluorescent sub-microsphere prepared emits the fluorescence with higher intensity during the fluorescence detection.

S500: Volatilization of the Organic Solvent

In some embodiments of the present disclosure, the second mixture is heated to volatilize the organic solvent, such that the fluorochrome is crystallized out and encapsulated in the nanopores, thus obtaining the near-infrared II polymer fluorescent sub-microsphere.

With slow volatilization of the organic solvent during heating, exterior of the polymer sub-microsphere is shrinked and the hydrophobic fluorochrome is crystallized out (forming hydrophobic pellets), so that the fluorochrome is encapsulated inside the polymer sub-microsphere. After the organic solvent is totally volatilized, the near-infrared II polymer fluorescent sub-microsphere is thus obtained, with the fluorochrome encapsulated inside barely with leakage.

In some embodiments of the present disclosure, the second mixture is heated at a temperature of 50° C. to 90° C., specifically 50° C., 55° C., 60° C., 65° C., 70° C., 75° C., 80° C., 85° C. or 90° C., preferably 50° C., so that the organic solvent, such as dichloromethane can be volatilized quickly and completely in a short time period, so as to improve the efficiency of the present method.

In some embodiments of the present disclosure, the second mixture is heated under magnetic stirring in a water bath at a temperature of 50° C. to 90° C., so that the dichloromethane in the sub-microsphere is volatilized in a high volatilizating rate, which improves the efficiency of the present method.

In some embodiments of the present disclosure, the method for preparing the near-infrared II polymer fluorescent sub-microsphere further includes subjecting the near-infrared II polymer fluorescent sub-microsphere obtained to ultrasonic cleaning with ethanol and water successively.

In some embodiments of the present disclosure, after dissolved in a certain quantity in dichloromethane, the near-infrared II polymer fluorescent sub-microsphere prepared by the present method is detected with its fluorescence intensity based on a standard curve, with a calculated result of around 80,000 fluorescent molecules encapsulated in each polymer sub-microsphere. Therefore, the near-infrared II polymer fluorescent sub-microsphere prepared can emit a greatly magnified fluorescence signal when applied in labeling detection as compared with small molecule fluorochrome, thereby improving sensitivity of the fluorescence detection.

Figure 4:
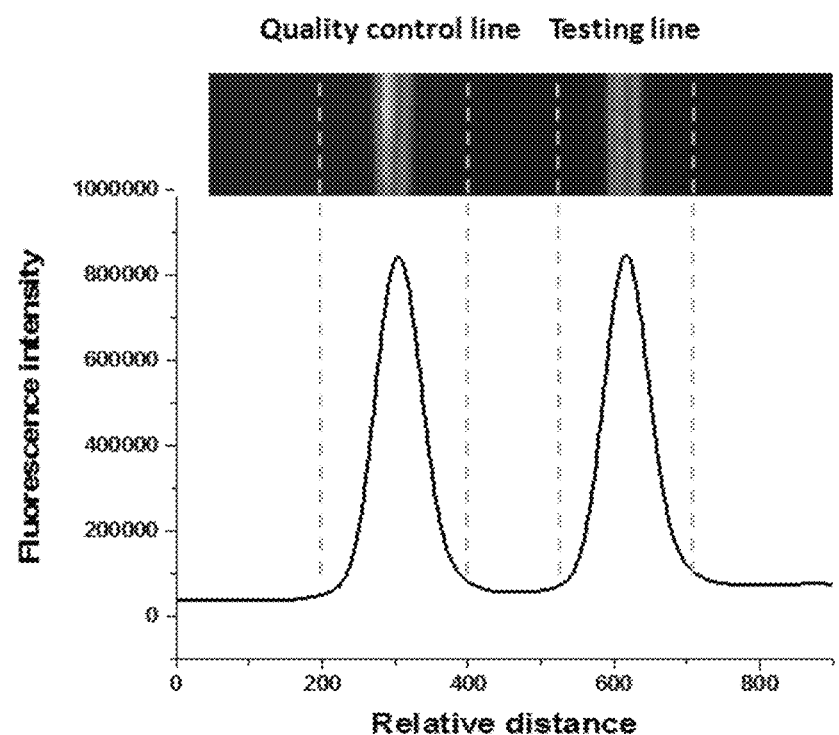
FIG. 4(A) shows a plot of fluorescent intensity as a function of Relative Distance.
FIG. 4(B) shows a plot of fluorescent intensity as a function of Relative Distance.
FIG. 4(C) shows a plot of fluorescent intensity as a function of Relative Distance.
Figure 4:
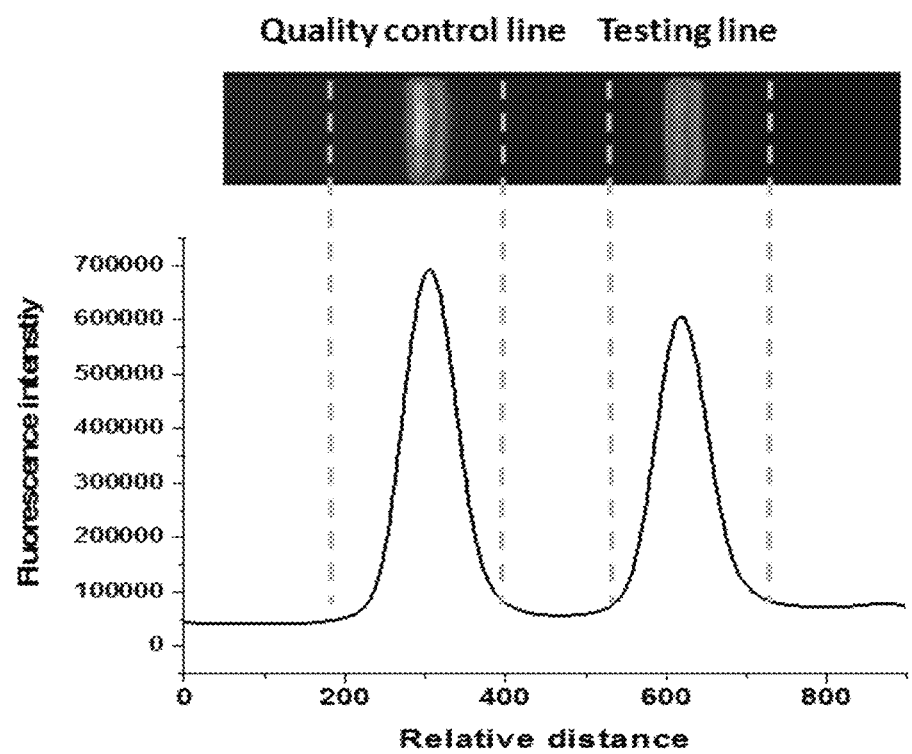
Figure 4:
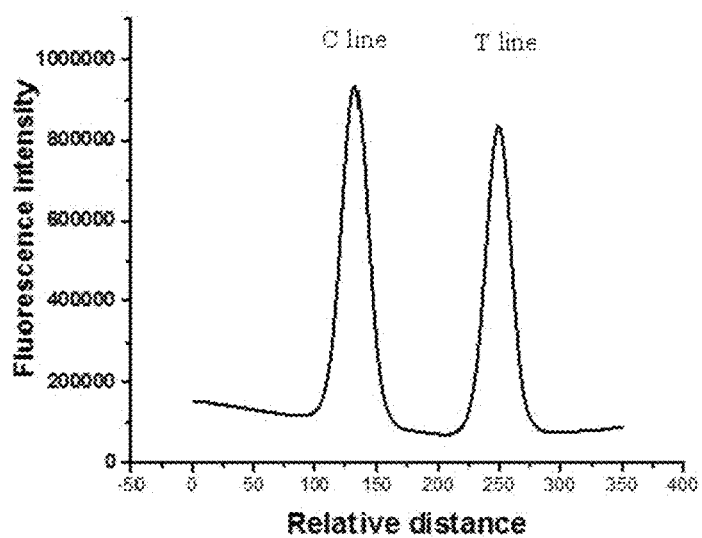

In some embodiments of the present disclosure, the present near-infrared II polymer fluorescent sub-microsphere is used to detect procalcitonin (PCT) in serum by immunochromatography detection. FIG. 4 (a) to (c) show results when the concentration of procalcitonin (PCT) in serum reaches 5 ng/ml. One result shows that the fluorescent signal in the testing line is very strong with extreme low background fluorescent signal (having a signal-to-noise ratio of 42). Thus, the near-infrared II polymer fluorescent sub-microsphere prepared by the present method can be applied in immunochromatography detection with high sensitivity.

In a second aspect, the present disclosure provides in embodiments a near-infrared II polymer fluorescent sub-microsphere prepared by the method described in the first aspect.

According to embodiments of the present disclosure, the near-infrared II polymer fluorescent sub-microsphere prepared has advantageous characteristics of good dispersibility, high quantum efficiency up to 25%, relative broader interval between an exciting wavelength at 740 nm and an emitting wavelength at 1000 nm to 1700 nm, and strong penetrability and low background interference during the fluorescence detection, thus dramatically magnifying a fluorescent signal and improving sensitivity of the fluorescence detection. Therefore, near-infrared II polymer fluorescent sub-microsphere prepared can be used in live imaging, biolabeling detection and so on with promising prospects.

The embodiments of the present disclosure will be described in detail by reference to the following examples.

It would be appreciated by those skilled in the art that the following examples are explanatory, and cannot be construed to limit the scope of the present disclosure. If the specific technology or conditions are not specified in the examples, a step will be performed in accordance with the techniques or conditions described in the literature in the art or in accordance with the product instructions. If the manufacturers of reagents or instruments are not specified, the reagents or instruments may be commercially available.

Example 1

(1) Synthesis of a Carboxyl Polystyrene Sub-Microsphere 190 ml of water was added into a 500 ml round bottom flask and then incubated in a water bath with a temperature of 70° C. under stirring at a speed of 350 rpm for half an hour. 16 mg of sodium dodecyl sulfate (SDS) as an emulsifier and 0.05 g of sodium bicarbonate as a buffer reagent were added and then incubated for another 10 minutes under the stirring. To the mixture, 8 ml of styrene and 0.8 ml of acrylic acid were further added. After one hour, 0.2 g of potassium persulfate was added and the obtained reaction mixture was subjected to polymerization reaction under nitrogen atmosphere for 18 hours. After completion of the reaction, the resulting product was centrifuged with a mixture of ethanol and water in a volume ratio of 2:1 (v/v) three times, thus obtaining the carboxyl polystyrene sub-microspheres. The scanning electron microscopy of such a sub-microsphere is shown in panel A of FIG. 6 (a). The carboxyl polystyrene sub-microspheres were distributed into a SDS solution at a concentration of 0.25% (w/v), thus obtaining a 30 mg/ml carboxyl polystyrene sub-microsphere dispersion as shown in FIG. 5 (A) which was stored in a refrigerator under 4° C. for the next step.

Figure 5:
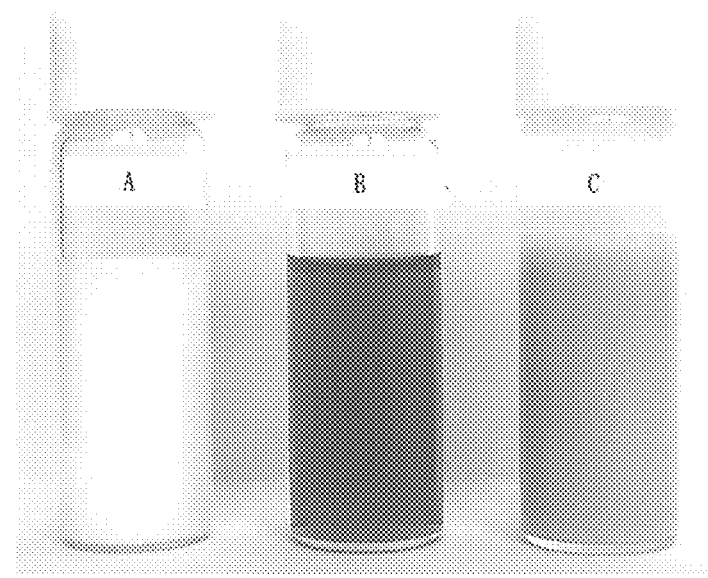
FIG. 5 is a photograph of materials used to make carboxyl polystyrene sub-microsphere dispersion.

(2) Synthesis of a Near-Infrared II Carboxyl Polystyrene Fluorescent Sub-Microsphere 40 mg of the near-infrared II fluorochrome represented by formula (I) was dissolved in 2 ml dichloromethane, thus obtaining a fluorochrome solution at a concentration of 20 mg/ml as shown in FIG. 5 (B). 20 ml of the carboxyl polystyrene sub-microsphere dispersion obtained in (1) was added into a 500 ml conical flask and subjected to ultrasonic treatment for 5 minutes, after which 2 ml fluorochrome solution obtained above was added and subjected to ultrasonic treatment, thus obtaining an emulsion. Then the emulsion was subjected to magnetic stirring at a temperature of 40° C. for 6 hours, such that the carboxyl polystyrene sub-microsphere swelled sufficiently and the fluorochrome solution entered nanopores formed during swelling of the polymer sub-microsphere. The mixture swelled was then subjected to magnetic stirring in a water bath at a temperature of 50° C. overnight, so as to volatilize the dichloromethane in the mixture completely. The product obtained was centrifuged, and then subjected to ultrasonic cleaning with ethanol three times and with water for several times until the supernatant of the product centrifuged contained no fluorochrome, thus obtaining the near-infrared II carboxyl polystyrene fluorescent sub-microsphere which was distributed into water in a weight/volume of 5% and stored in a refrigerator under 4° C. for the next step (FIG. 5 (C)).

(3) Evaluation of the Near-Infrared II Carboxyl Polystyrene Fluorescent Sub-Microsphere Obtained in (2)

3.1 In FIG. 5, FIG. 5 (A) shows that the solution of carboxyl polystyrene in SDS is white, FIG. 5 (B) shows that the solution of fluorochrome represented by formula (I) in dichloromethane is cyan, and FIG. 5 (C) shows that the solution of carboxyl polystyrene fluorescent sub-microsphere encapsulating the fluorochrome represented by formula (I) is also cyan. Thus, it is demonstrated that the fluorochrome was successfully encapsulated in the sub-microsphere and properties on the surface of the sub-microsphere have not been changed significantly according to the color change. It also can be seen from the FIG. 5 (C) that the near-infrared II carboxyl polystyrene fluorescent sub-microsphere obtained can be distributed into water uniformly and stably.

Figure 6:
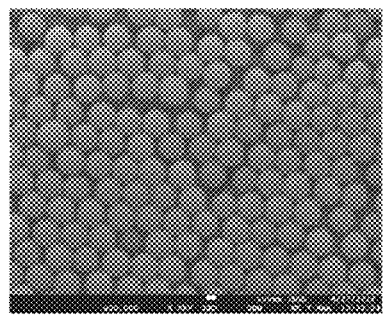
FIG. 6(A) show polymer sub-microspheres.
FIG. 6(B)—parts A and B—show polymer sub-microspheres.
FIG. 6(C)—parts A and B—show polymer sub-microspheres.
Figure 6:
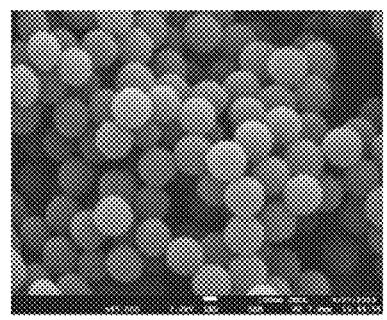
Figure 6:
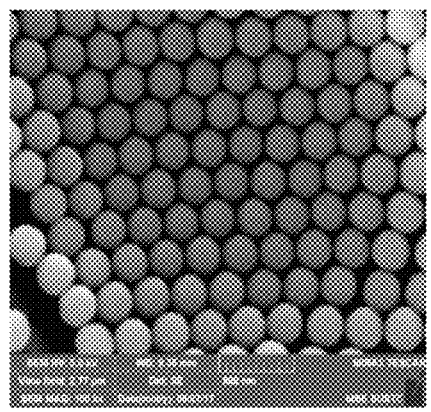
Figure 6:
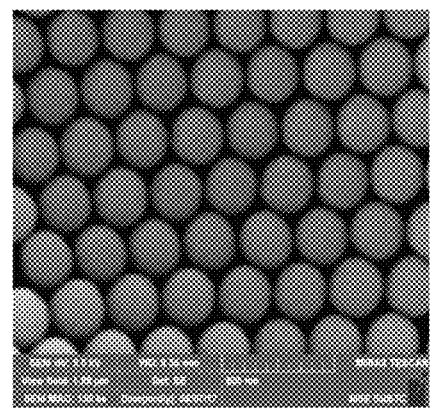
Figure 6:
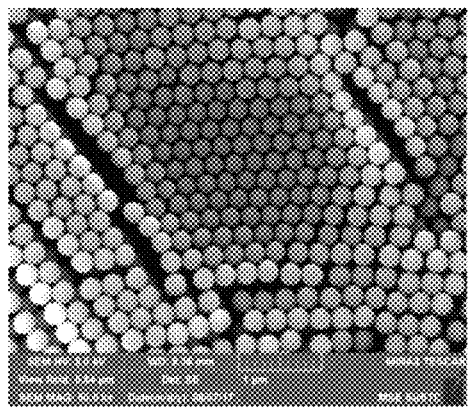
Figure 6:
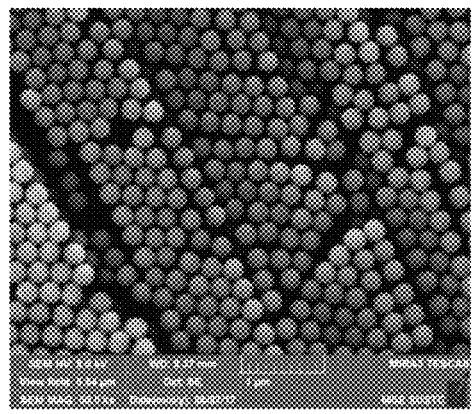

3.2 Panel B of FIG. 6 (*a*) shows a scanning electron microscope photograph of the near-infrared II carboxyl polystyrene fluorescent sub-microsphere obtained in (2). It can be seen from FIG. 6 (*a*) that morphology of the carboxyl polystyrene sub-microsphere has not been changed significantly before and after encapsulation of the fluorochrome, and the fluorescent sub-microspheres obtained are uniform in size and are not aggregated together.

Figure 7:
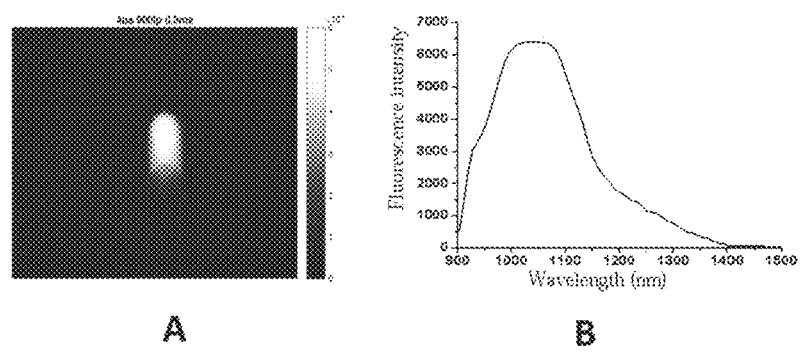
FIG. 7(A)—parts A and B—show a fluorescence image and a plot of fluorescence intensity as a function of wavelength.
FIG. 7(B) shows a plot of absorption and emission as a function of wavelength.
FIG. 7(C) shows a plot of emission as a function of wavelength.
Figure 7:
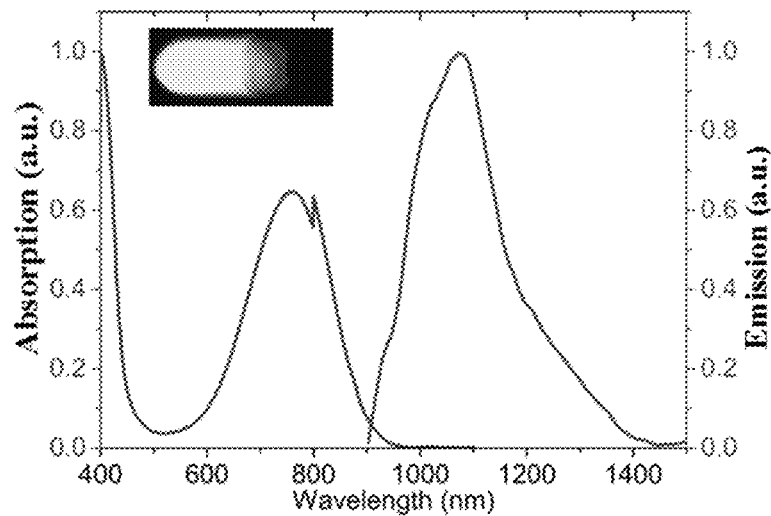
Figure 7:
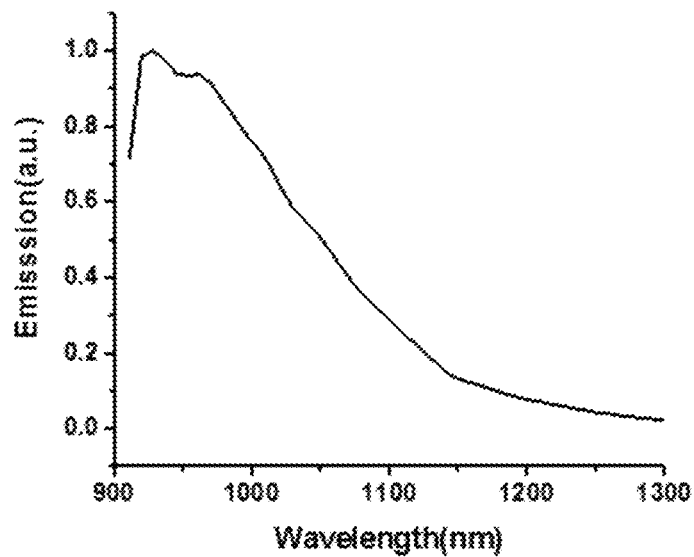

3.3 Panel A of FIG. 7 (*a*) shows a fluorescent photograph of the carboxylic polystyrene fluorescent sub-microsphere obtained in (2) under irradiation with an excitation light at a wavelength of 740 nm, and panel 13 of FIG. 7 (*a*) shows its fluorescent spectrum. It can be seen from the FIG. 7 (*a*) that the carboxylic polystyrene fluorescent sub-microsphere can emit fluorescence in a wavelength between 800 nm to 1700 nm with high fluorescence intensity, and its fluorescence quantum yield reaches 25% based on measurement.

(4) Application of the Near-Infrared II Carboxyl Polystyrene Fluorescent Sub-Microsphere Obtained in (2)

4.1 Coupling an Antibody to the Near-Infrared II Carboxyl Polystyrene Fluorescent Sub-Microsphere The near-infrared II carboxyl polystyrene fluorescent sub-microsphere obtained in (2) was distributed into a 2-morpholinoethanesulfonic acid (MES) buffer (10 mM, pH 6.2), thus obtaining a uniform dispersion in a weight/volume ratio of 1%. To the dispersion, 1-ethyl-3-(3-dimethylaminopropyl)carbodiimide (EDC) buffer (5 mg/ml) and sulfo-(N-hydroxysulfosuccinimide) (sulfo-NHS) buffer (5 mg/ml) were added for activation for 15 minutes. After centrifugation, the supernatant was discarded and the remaining mixture was distributed into the MES buffer (10 mM, pH 6.5) again. And then 0.2 mg/ml of Mouse Monoclonal Antibody (anti-PCT1 (MJG 05, Hangzhou Qitai biotechnology Co., LTD)) was added and incubated for 2 hours under stirring. The resulting mixture was centrifuged again, the supernatant was discarded and the remaining pellets were distributed into 20 mM PBS containing 0.5% casein, 2.5% BSA, 1% sugar, 2% PEG-2000 and 0.03 wt % $NaN_3$ (pH 8.0) under ultrasonic treatment, thus obtaining a fluorescent sub-microsphere dispersion coupled with antibody anti-PCT1 (1%, w/v) which was stored in a refrigerator under 4° C. for the next step.

4.2 Preparation of a Strip for an Immunofluorescence Chromatographic Test

The fluorescent sub-microsphere dispersion coupled with antibody (anti-PCT1) obtained in the above step was sprayed uniformly onto a binding pad by a sprayer specialized for immunofluorescence chromatographic test, and subjected to lyophilization for 10 hours and then stored for future use. 75 µL of anti-PCT2 solution (1.0 mg/ml) (MJG 03, Hangzhou Qitai biotechnology Co., LTD) was sprayed uniformly on to a part of a nitrocellulose membrane by a scriber specialized for immunofluorescence chromatographic test, thus obtaining a testing line (i.e., T line); as the similar way, 75 µL of goat-anti-mouse antibody solution (1.2 mg/ml) (Hangzhou Qitai biotechnology Co., LTD) was sprayed uniformly onto another part of the nitrocellulose membrane by the scriber, thus obtaining a quality control line (i.e., C line), after which the nitrocellulose membrane was incubated at a temperature of 37° C. in an oven overnight. Then a sample pad, the binding pad, the nitrocellulose membrane and an adsorbing pad together were fixed neatly onto a hard cardboard along the axis direction. Finally, the chromatoplate assembled was cut into strips in a width of 3 mm by a cutter for an immunofluorescence chromatographic strip. The strip obtained was packaged into an aluminium bag for storage.

4.3 Quantitative Detection by the Strip for the Immunofluorescence Chromatographic Test 75 µL of human serum was applied onto the sample pad of the strip and moved toward the adsorbing pad of the strip by capillary force. After 15 minutes, the strip was imaged in the near-infrared imaging system for quantitative detection.

Example 2

(1) Synthesis of a Carboxyl Polystyrene Sub-Microsphere

All steps for synthesizing a carboxyl polystyrene sub-microsphere are same as those in Example 1. The scanning electron microscopy of the carboxyl polystyrene sub-microsphere obtained is shown in panel A of FIG. 6 (*b*) and a carboxyl polystyrene sub-microsphere dispersion obtained is same as that shown in FIG. 5 (A).

(2) Synthesis of a Near-Infrared II Carboxyl Polystyrene Fluorescent Sub-Microsphere All steps for synthesizing a near-infrared II carboxyl polystyrene fluorescent sub-microsphere are similar with those in Example 1, except that the near-infrared II fluorochrome is represented by formula (II).

(3) Evaluation of the Near-Infrared II Carboxyl Polystyrene Fluorescent Sub-Microsphere Obtained in (2)

All steps for evaluating the near-infrared II carboxyl polystyrene fluorescent sub-microsphere obtained are same as those in Example 1.

3.1 The solution of fluorochrome represented by formula (II) in dichloromethane is also cyan, as shown in FIG. 5 (B); and the solution of carboxyl polystyrene fluorescent sub-microsphere encapsulating the fluorochrome represented by formula (II) is also cyan, as shown in FIG. 5 (C). It also can be seen from the FIG. 5 (C) that the near-infrared II carboxyl polystyrene fluorescent sub-microsphere obtained can be distributed into water uniformly and stably.

3.2 Panel B of FIG. 6 (*b*) shows a scanning electron microscope photograph of the near-infrared II carboxyl polystyrene fluorescent sub-microsphere obtained in (2). It can be seen from FIG. 6 (*b*) that morphology of the carboxyl polystyrene sub-microsphere has not been changed significantly before and after encapsulation of the fluorochrome represented by formula (II), and the fluorescent sub-microspheres obtained are uniform in size and are not aggregated together.

3.3 A fluorescent photograph of the carboxylic polystyrene fluorescent sub-microsphere obtained in (2) and its fluorescent spectrum are shown in FIG. 7 (*b*), which indicates that the carboxylic polystyrene fluorescent sub-microsphere can emit fluorescence in a wavelength between 800 nm to 1700 nm with high fluorescence intensity, and its fluorescence quantum yield reaches 25% based on measurement.

(4) Application of the Near-Infrared II Carboxyl Polystyrene Fluorescent Sub-Microsphere Obtained in (2)

All the steps for the application of the near-infrared II carboxyl polystyrene fluorescent sub-microsphere obtained in (2) are same as those in Example 1.

Example 3

(1) Synthesis of a Carboxyl Polystyrene Sub-Microsphere

All steps for synthesizing a carboxyl polystyrene sub-microsphere are same as those in Example 1. The scanning electron microscopy of the carboxyl polystyrene sub-microsphere obtained is shown in panel A of FIG. 6 (*c*) and a carboxyl polystyrene sub-microsphere dispersion obtained is same as that shown in FIG. 5 (A).

(2) Synthesis of a Near-Infrared II Carboxyl Polystyrene Fluorescent Sub-Microsphere All steps for synthesizing a near-infrared II carboxyl polystyrene fluorescent sub-microsphere are similar with those in Example 1, except that the near-infrared II fluorochrome is represented by formula (III).

(3) Evaluation of the Near-Infrared II Carboxyl Polystyrene Fluorescent Sub-Microsphere Obtained in (2)

All steps for evaluating the near-infrared II carboxyl polystyrene fluorescent sub-microsphere obtained are same as those in Example 1.

3.1 The solution of fluorochrome represented by formula (III) in dichloromethane is also cyan, as shown in FIG. 5 (B); and the solution of carboxyl polystyrene fluorescent sub-microsphere encapsulating the fluorochrome represented by formula (III) is also cyan, as shown in FIG. 5 (C). It also can be seen from the FIG. 5 (C) that the near-infrared II carboxyl polystyrene fluorescent sub-microsphere obtained can be distributed into water uniformly and stably.

3.2 Panel B of FIG. 6 (*c*) shows a scanning electron microscope photograph of the near-infrared II carboxyl polystyrene fluorescent sub-microsphere obtained in (2). It can be seen from FIG. 6 (*c*) that morphology of the carboxyl polystyrene sub-microsphere has not been changed significantly before and after encapsulation of the fluorochrome represented by formula (III), and the fluorescent sub-microspheres obtained are uniform in size and are not aggregated together.

3.3 A fluorescent spectrum of the carboxylic polystyrene fluorescent sub-microsphere obtained in (2) is shown in FIG. 7 (*c*), which indicates that the carboxylic polystyrene fluorescent sub-microsphere can emit fluorescence in a wavelength between 800 nm to 1700 nm with high fluorescence intensity, and its fluorescence quantum yield reaches 25% based on measurement.

(4) Application of the Near-Infrared II Carboxyl Polystyrene Fluorescent Sub-Microsphere Obtained in (2)

All the steps for the application of the near-infrared II carboxyl polystyrene fluorescent sub-microsphere obtained in (2) are same as those in Example 1.

Throughout this specification, reference to "an embodiment", "some embodiments", "one embodiment", "another example", "an example", "a specific example" or "some examples" means that a particular feature, structure, material or characteristic described in connection with the embodiment or example is included in at least one embodiment or example of the present disclosure. Thus, the appearances of the phrases such as "in some embodiments", "in one embodiment", "in an embodiment", "in another example", "in an example", "in a specific example" or "in some examples" in various places throughout this specification are not necessarily referring to the same embodiment or example of the present disclosure. Furthermore, the particular features, structures, materials or characteristics may be combined in any suitable manner in one or more embodiments or examples. In addition, it will be apparent to those skilled in the art that different embodiments or examples as well as features of the different embodiments or examples described in this specification may be combined without contradictory.

Although explanatory embodiments have been shown and described, it would be appreciated by those skilled in the art that the above embodiments cannot be construed to limit the present disclosure, and changes, alternatives and modifications can be made in the embodiments without departing from spirit, principles and scope of the present disclosure.

The invention claimed is:

1. A method for preparing a near-infrared II polymer fluorescent sub-microsphere, comprising the following steps of:
   1) Dissolving fluorochrome in a water-immiscible organic solvent, thus obtaining a fluorochrome solution;
   2) Distributing a polymer sub-microsphere into a sodium dodecyl sulfonate solution, thus obtaining a sub-microsphere solution with the polymer sub-microsphere as a carrier for the fluorochrome;
   3) Subjecting a first mixture of the fluorochrome solution and the sub-microsphere solution to ultrasonic treatment, thus obtaining an emulsion;
   4) Swelling the emulsion such that the fluorochrome solution enters nanopores formed during swelling of the polymer sub-microsphere, thus obtaining a second mixture; and
   5) Heating the second mixture to volatilize the organic solvent, such that the fluorochrome is crystallized out and encapsulated in the nanopores, thus obtaining the near-infrared II polymer fluorescent sub-microsphere, wherein the near-infrared II polymer fluorescent sub-microsphere obtained by steps 1) to 5) results in emitting a wavelength in a range of 1000 nm to 1700 nm under an excitation light less than 1000 nm.

2. The method according to claim 1, wherein the fluorochrome emits a wavelength in a range of 1000 nm to 1700 nm under an excitation light less than 1000 nm.

3. The method according to claim 2, wherein the fluorochrome is selected from the group consisting of organic molecules including those shown as formula (I), formula (II) or formula (III), or carbon nanotubes, or PbS, PbSe or InAs quantum dots, or rare earth nanoparticles 6. The method according to claim 1, wherein the polymer sub-microsphere is at least one selected from the group consisting of polystyrene sub-microspheres, poly (methyl methacrylate) sub-microspheres, polyformaldehyde sub-microspheres and poly(lactic acid-co-glycolic acid) sub-microspheres.

7. The method according to claim 1, wherein the polymer sub-microsphere has a particle size of 20 nm to 1000 nm.

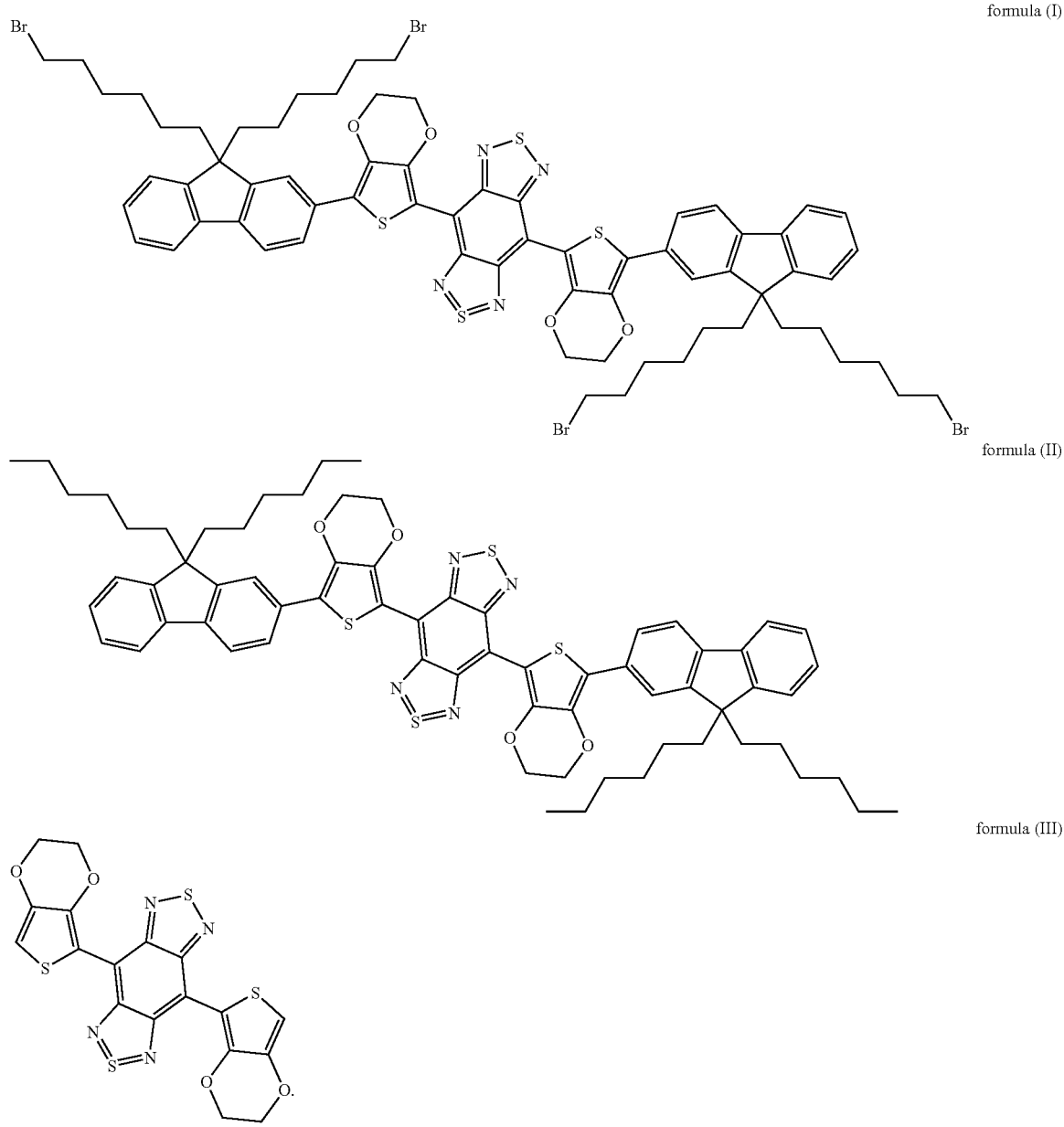 [SMILES: BrCCCCCCC1(CCCCCCBr)c2ccccc2-c2ccc(-c3sc(-c4c5c(c(-c6sc(-c7ccc8c(c7)C(CCCCCCBr)(CCCCCCBr)c7ccccc7-8)c7c6OCCO7)c6nsnc46)N=S=N5)c4c3OCCO4)cc21 ; CCCCCCC1(CCCCCC)c2ccccc2-c2ccc(-c3sc(-c4c5c(c(-c6sc(-c7ccc8c(c7)C(CCCCCC)(CCCCCC)c7ccccc7-8)c7c6OCCO7)c6nsnc46)N=S=N5)c4c3OCCO4)cc21 ; c1sc(-c2c3c(c(-c4scc5c4OCCO5)c4nsnc24)N=S=N3)c2c1OCCO2]

4. The method according to claim 1, wherein the fluorochrome in the fluorochrome solution has a concentration of 1 to 50 mg/ml.

5. The method according to claim 1, wherein the organic solvent is at least one selected from the group consisting of ethyl acetate, trichloromethane, 1,2-dichloroethane aromatic hydrocarbons, and dichloromethane.

8. The method according to claim 1, wherein in the step 2), the polymer sub-microsphere is distributed into the sodium dodecyl sulfonate solution in a mass/volume ratio of 10 mg/ml to 200 mg/ml.

9. The method according to claim 1, wherein in the step 3), the first mixture comprises the fluorochrome solution and the sub-microsphere solution in a volume ratio of 1:5 to 1:20.

10. The method according to claim 1, wherein in the step 3), the first mixture comprises the fluorochrome and the polymer sub-microsphere in a mass ratio of 0.1:100 to 30:100.

11. The method according to claim 1, wherein in the step 4), the emulsion is swelled at 10° C. to 50° C. under stirring for 1 hour to 10 hours.

12. The method according to claim 1, wherein in the step 5), the second mixture is heated at a temperature of 50° C. to 90° C.

13. A near-infrared II polymer fluorescent sub-microsphere prepared by the method according to claim 1.

14. A near-infrared II polymer fluorescent sub-microsphere, comprising hydrophobic fluorochrome and a polymer sub-microsphere, wherein
the fluorochrome is encapsulated in nanopores of the polymer sub-microsphere, and
the polymer sub-microsphere is of hydrophobic moiety inside and hydrophilic moiety outside; and
the near-infrared II polymer fluorescent sub-microsphere emits a wavelength in a range of 1000 nm to 1700 nm under an excitation light less than 1000 nm.

15. The near-infrared II polymer fluorescent sub-microsphere of claim 14, wherein the fluorochrome is selected from the group consisting of organic molecules including those shown as formula (I), formula (II) or formula (III), or carbon nanotubes, or PbS, PbSe or InAs quantum dots, or rare earth nanoparticles

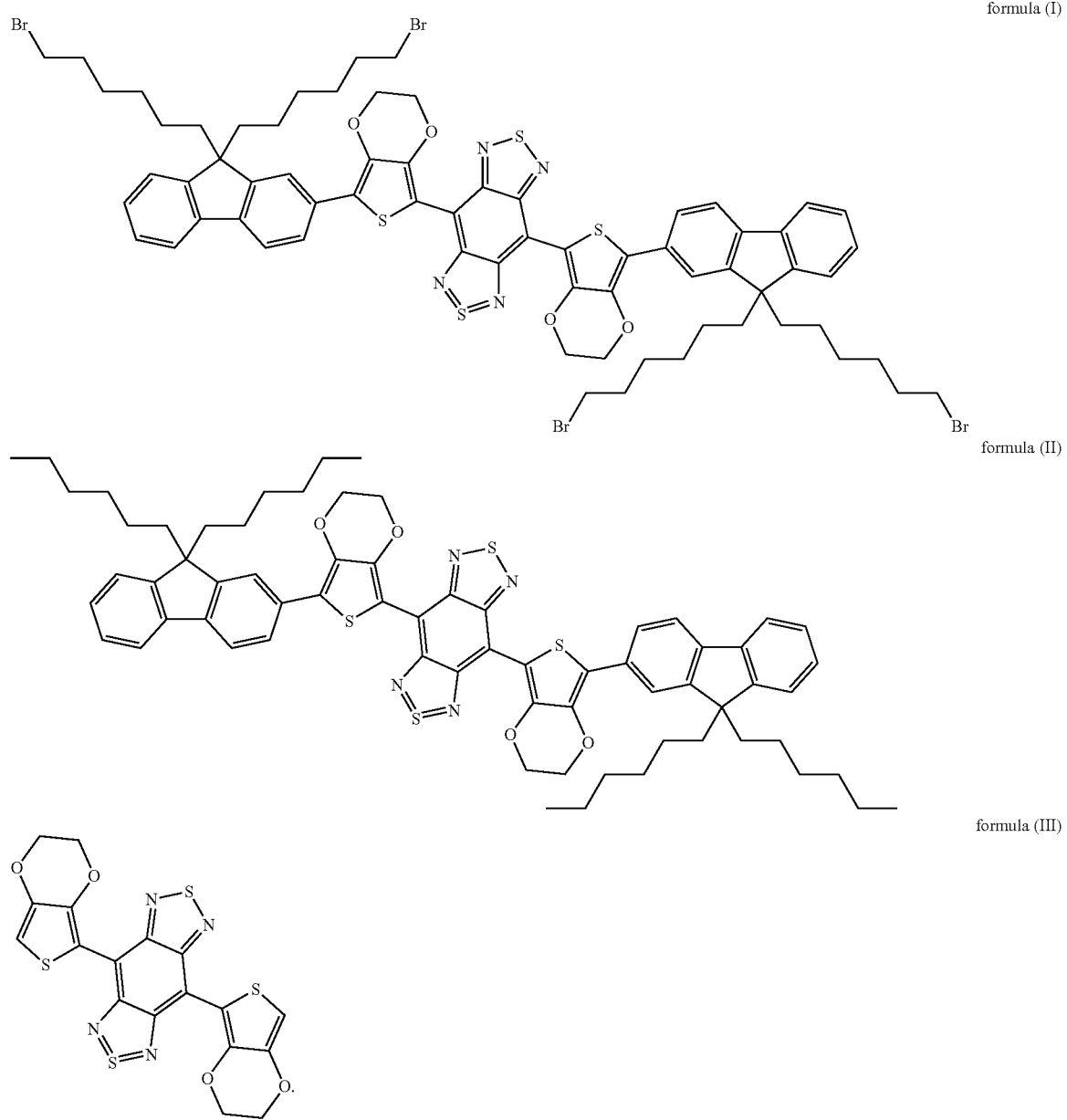 [SMILES: BrCCCCCCC1(CCCCCCBr)c2ccccc2-c2ccc(-c3sc(-c4c5c(c(-c6sc(-c7ccc8c(c7)C(CCCCCCBr)(CCCCCCBr)c7ccccc7-8)c7c6OCCO7)c6nsnc46)N=S=N5)c4c3OCCO4)cc21 ; CCCCCCC1(CCCCCC)c2ccccc2-c2ccc(-c3sc(-c4c5c(c(-c6sc(-c7ccc8c(c7)C(CCCCCC)(CCCCCC)c7ccccc7-8)c7c6OCCO7)c6nsnc46)N=S=N5)c4c3OCCO4)cc21 ; c1sc(-c2c3c(c(-c4scc5c4OCCO5)c4nsnc24)N=S=N3)c2c1OCCO2]

16. The near-infrared II polymer fluorescent sub-microsphere of claim 14, wherein the polymer sub-microsphere is at least one selected from the group consisting of polystyrene sub-microspheres, poly (methyl methacrylate) sub-microspheres, polyformaldehyde sub-microspheres and poly (lactic acid-co-glycolic acid) sub-microspheres.

17. The near-infrared II polymer fluorescent sub-microsphere of claim 14, wherein the polymer sub-microsphere has a particle size of 20 nm to 1000 nm.

* * * * *